United States Patent
Schade et al.

(10) Patent No.: US 9,410,661 B2
(45) Date of Patent: Aug. 9, 2016

(54) HOLDING DEVICE AND MEDICAL DEVICE FOR EXTRACORPOREAL BLOOD TREATMENT INCLUDING HOLDING DEVICE

(71) Applicant: B. BRAUN AVITUM AG, Melsungen (DE)

(72) Inventors: Andreas Schade, Rotenburg (DE); Bruno Stenzel, Hatten (DE)

(73) Assignee: B. Braun Avitum AG, Melsungen (DE)

( * ) Notice: Subject to any disclaimer, the term of this patent is extended or adjusted under 35 U.S.C. 154(b) by 572 days.

(21) Appl. No.: 13/933,659

(22) Filed: Jul. 2, 2013

(65) Prior Publication Data

US 2014/0008507 A1  Jan. 9, 2014

(30) Foreign Application Priority Data

Jul. 3, 2012 (DE) .......................... 10 2012 105 912

(51) Int. Cl.
| | |
|---|---|
| *F16M 13/02* | (2006.01) |
| *F16M 11/10* | (2006.01) |
| *F16M 11/06* | (2006.01) |
| *A61B 19/10* | (2006.01) |
| *A61M 1/16* | (2006.01) |
| *A61G 7/05* | (2006.01) |

(52) U.S. Cl.
CPC .............. *F16M 13/022* (2013.01); *A61B 50/20* (2016.02); *A61M 1/16* (2013.01); *F16M 11/06* (2013.01); *F16M 11/10* (2013.01); *F16M 11/105* (2013.01); *A61G 7/0503* (2013.01); *A61M 2209/082* (2013.01)

(58) Field of Classification Search
CPC .. A61B 19/0256; A61B 50/20; A61G 7/0503; A61M 1/16; A61M 2209/082; F16M 13/022; F16M 11/06; F16M 11/10; F16M 11/105
See application file for complete search history.

(56) References Cited

U.S. PATENT DOCUMENTS

| | | | |
|---|---|---|---|
| 3,737,130 A | | 6/1973 | Shiraishi |
| 5,641,144 A | * | 6/1997 | Hendrickson ........... A61M 1/16 128/DIG. 26 |

(Continued)

FOREIGN PATENT DOCUMENTS

| | | |
|---|---|---|
| DE | 517875 | 1/1931 |
| DE | 2 048 592 | 2/1972 |

(Continued)

OTHER PUBLICATIONS

German Search Report for DE 10 2012 105 912 dated Apr. 29, 2013.

(Continued)

*Primary Examiner* — John Kim
(74) *Attorney, Agent, or Firm* — RatnerPrestia

(57) ABSTRACT

Holding devices for a medical device including a holder and a second component part by which the holder is coupled or adapted to be coupled are disclosed. The holder has a receiving portion into which a functional member can be detachably introduced. The holder further includes a pivot portion about which the holder is pivoted about an axis of rotation to a support of the second component part, wherein the support is movable vis-à-vis the second component part in a spring-loaded manner. The second component part includes a recess within which the pivot portion and the support are arranged so that upon pivoting the holder about the axis of rotation merely the receiving portion protrudes from the recess. Medical devices for extracorporeal blood treatment including a holding device of this type are also disclosed.

10 Claims, 3 Drawing Sheets

(56) References Cited

U.S. PATENT DOCUMENTS

2004/0046487 A1* 3/2004 Olivera .............. A61B 19/0248
312/209
2007/0252057 A1 11/2007 Utterberg et al.

FOREIGN PATENT DOCUMENTS

| DE | 29 52 660 | 7/1981 |
|----|-----------|--------|
| DE | 87 02 995 | 5/1987 |
| DE | 101 64 368 | 6/2003 |
| EP | 1 396 235 | 3/2004 |
| FR | 2 310 136 | 12/1976 |
| WO | WO 96/40315 | 12/1996 |

OTHER PUBLICATIONS

European Search Report for EP13174677.8 dated Sep. 26, 2013.

* cited by examiner

HOLDING DEVICE AND MEDICAL DEVICE FOR EXTRACORPOREAL BLOOD TREATMENT INCLUDING HOLDING DEVICE

CROSS REFERENCE TO RELATED APPLICATION

This application claims priority to German Patent Application No. DE 10 2012 105 912.8, filed Jul. 3, 2012, the contents to such application being incorporated by reference herein.

FIELD OF THE INVENTION

The invention relates to a holding device for a medical device comprising a holder and a second component part on which the holder is mounted, wherein the holder includes a receiving portion to which a functional member can be detachably introduced.

The invention further relates to a medical device for extracorporeal blood treatment comprising such holding device.

BACKGROUND INFORMATION

In medical devices with extracorporeal blood circulation, i.e. especially in medical devices for blood purification, filters permitting the substance exchange are used. Said filters can be fastened or held at the medico-technical device. For reasons of handling said holders are conventionally arranged at exposed positions and are configured to be movable.

Frequently, said holders are in the form of a removable accessory and have to be mounted at an appropriate position by the operator of the device. However, this entails the risk of the holder being arranged at an inappropriate position or being used in a not intended manner. Furthermore it is possible that the holder is removed from the device and then the device cannot be operated.

If the holder is rigidly connected to the housing of the device, however, there is a risk that the holder is dismounted when bottlenecks such as door frames are passed and that in this way damage of the medico-technical device occurs.

SUMMARY OF THE INVENTION

Therefore it is the object of the invention to provide a robust support for a medical functional member which prevents faulty operations.

It is a further object of the invention to provide a medical device for extracorporeal blood treatment including such support.

The holding device for a medical device according to aspects of the invention includes a holder and a second component part on which the holder is mounted or to which the holder can be coupled, respectively, wherein the holder includes a receiving portion to which a functional member can be detachably introduced or connected. The second component part has a recess inside of which a support movable vis-à-vis the second component part in a spring-loaded manner is arranged. The holder in turn is pivoted about an axis of rotation to the support, wherein a tensile force can be applied to the holder by the spring-loaded support. Furthermore the holder or the recess is configured such that upon pivoting the holder about the axis of rotation a pivoting portion of the holder moves within the recess while the receiving portion protrudes from the recess.

This design of a holding device can increase the ruggedness of the same, for the resilient connection of the holder to the second component part protects both component parts from damage. In addition, the holder can be pivoted about an axis of rotation which can be brought about with intent but also unintentionally. Intended pivoting motions permit the well-directed positioning of the holder at a particular position and in the case of unintended impacts the holder deviates without any fractures or breaks occurring in component parts.

When the second component part is a medical device for extracorporeal blood treatment or the housing of such medical device, for example, a dialyser or a holder for receiving a dialyser can be mounted on the holding device. When bottlenecks are passed, the holder cannot be pulled off and the medico-technical device is not damaged. Only the receiving portion protrudes from the housing, while the pivoting portion is largely provided inside the recess in the housing and thus can close off the housing to the outside. The area between the pivoting portion of the holder and the recess may be bridged by a cover or is even sealed by a sealing.

By the holding device according to aspects of the invention a holder for accommodating a functional member can be integrated in the field of handling of an operator at a suited position, whereby faulty operations are prevented. The holder is moreover integrated in the second component part in such manner that it cannot be removed. The operation of a medical device thus cannot be impaired by a missing holder. Furthermore, it is also possible to integrate further elements such as tube holders into the holder so as to be able to accommodate e.g. drip chambers and/or tubes.

In an embodiment of the invention the second component part includes means for delimiting pivoting of the holder between two defined end positions. For this, at the second component part for example two stops can be formed each of which contacts a stop face at the pivoting portion of the holder at the two defined end positions. Thus the holder cannot be pivoted beyond the end positions. The stops may be designed, however, so that they stop the pivoting motion of the holder before the latter contacts housing parts which otherwise might be damaged. This is especially the outer rim of the recess in the housing inside which the holding device is arranged. For, if the holder abuts against the rim during pivoting, breaking might be entailed.

The holder can be movably mounted on the second component part via a connecting bolt or pivot bolt, for instance, which is guided through an eye of the support, each of the two end portions of the connecting bolt being introduced in a receiving portion at the second component part. In this way an axis of rotation can be formed about which the holder is pivotable. In an embodiment of the invention, the receiving portions are provided at a bolting plate that is detachably mounted on the second component part. Such bolting plate especially has the advantage that the required geometry of the holding device need not be formed in the housing, which facilitates the manufacture of the housing. Rather, the bolting plate can be appropriately shaped and bolted to the housing. The bolting plate can also be made of a material different from that of the second component part and/or the holder.

In another embodiment of the invention, a friction brake by which the pivoting motion of the holder about the axis of rotation can be decelerated is provided at the holding device. This has the advantage that both intended and unintended pivoting motions are decelerated, which further reduces the risk of damage of a component. In order to realize a friction brake at least two plate- or disk-shaped braking elements can be formed at the pivot portion so that they are in permanent contact with the support upon pivoting the holder, wherein the braking elements contact the support on two opposed sides and extend transversely to the axis of rotation.

Furthermore, aspects of the invention include a medical device for extracorporeal blood treatment including a housing and a holding device including a holder for accommodating a functional part of the medical device, the holding device being configured according to the invention. The functional part to be accommodated then can be a dialyser, for example, or a further holder for accommodating the dialyser. Such medical device can make use of the advantages of the holding device according to the invention and is especially protected against damage. However, the holding device can also be provided at other medical devices in which a robust support for a functional member is to be provided.

BRIEF DESCRIPTION OF THE DRAWINGS

The invention is best understood from the following detailed description when read in connection with the accompanying drawings. Included in the drawings are the following figures.

DETAILED DESCRIPTION OF EMBODIMENTS

Figure 1:
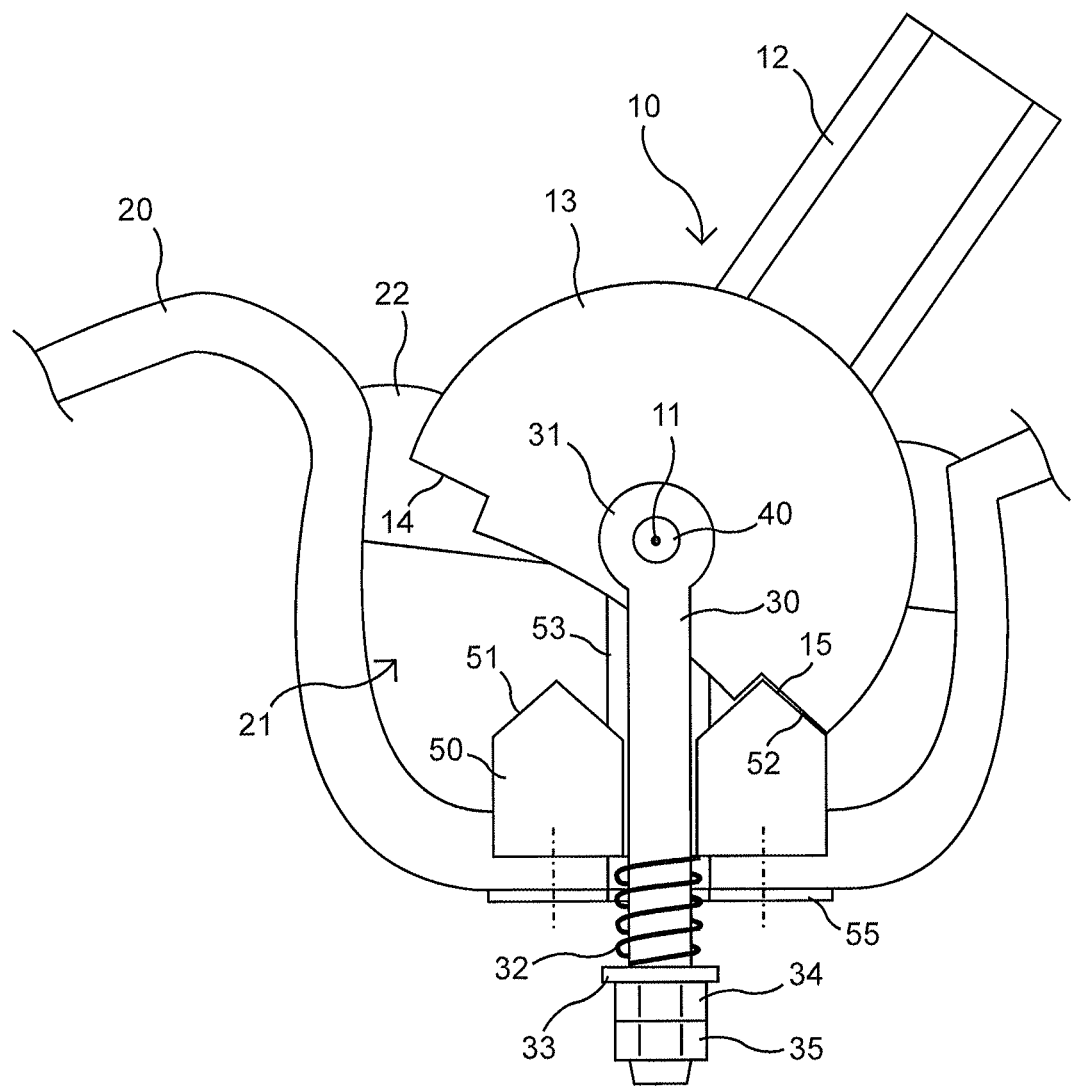
FIG. 1 a schematic section across the pivot axis of an embodiment of the holding device according to the invention, the holder abutting against a first end position.

FIG. 1 shows an embodiment of a holding device according to the invention integrated in a second component part 20. The second component part 20 is the housing of a medical device, for example, being especially a medical device for extracorporeal blood treatment to which a functional member such as a filter or dialyser is mounted for therapy. The invention is to be described by the Figures by way of such device for extracorporeal blood treatment, but the holding device can also be used for other medical devices on which functional members are to be detachably mounted.

FIG. 1 shows a schematic section across the pivot axis 11 of a holder 10, wherein only the cut-out of the housing 20 is shown in which the support 30 is arranged. This can be, for example, the corner area of a housing.

The holding device comprises the holder 10 arranged to directly or indirectly accommodate a functional member of the medical device. For this, at the holder 10 a receiving portion 12 is provided which in the shown embodiment is configured so that a filter holder can be inserted into the hollow-cylindrical receiving portion 12. The dialyser then can be introduced into said filter holder. Such filter holder may be locked axially inside the receiving portion 12 but may be simultaneously pivoted so that the filter holder can be rotated inside the receiving portion 12.

However, the receiving portion 12 can also be directly configured as a filter holder into which a dialyser can be detachably introduced so that after use the filter can be removed from the holding device again. The holder 10 may be formed of plastic material. Furthermore, a compartment holder and/or a tube holder can be additionally mounted or integrally formed on the holder 10.

The holding device comprises a recess 21 in which the holder 10 is movably integrated. In the embodiment of the figures, the recess 21 is provided in a corner area of the housing 20 so that said corner is in the form of a holding device. The holder 10 is divided into a pivot portion 13 and the receiving portion 12, the pivot portion 13 being provided inside or at least largely inside the recess 21, whereas the receiving portion 12 protrudes from the recess 21. The pivot portion 13 closes against the housing 20 via a cover 22. Said cover can also have a sealing effect so that it can also be considered to be a sealing.

The holder 10 is pivoted via an axis of rotation 11 to a support 30 which in turn is movable vis-à-vis the housing 20 in a spring-loaded manner. The support is designed, for example, as an eye bolt 30 through the eye 31 of which a connecting bolt or pivot bolt 40 is guided. The connection of said connecting bolt 40 to the housing 20 is also evident from FIG. 3 in a different view.

In an embodiment of the invention, the eye bolt 30 is guided with its free end through a bore in the bolting plate or mounting member 50 arranged at the housing 20 and protrudes into an opening in the recess 21. From inside a plate-shaped sheet member 55 can be positioned at the housing 20 so that a screwed connection can be guided through said sheet member 55 and the housing 20 into the bolting plate 50. The housing 20 is thus clamped between the bolting plate 50 and the sheet member 55. The sheet member 55 possibly improves the stability of the connection depending on the material of the bolting plate 50 and the housing 20. The connection between the bolting plate 50 and the housing 20 can also be configured in other ways so that the housing 20 may be appropriately formed in this area so as to be able to mount the bolting plate 50 in a suitable manner.

On the other side of the bolting plate 50 the eye bolt 30 is surrounded by a compression spring 32 which together with a stop at the end of the eye bolt 30 applies a tensile force to the eye bolt 30 which attracts the holder 10 to the housing 20, as the spring 32 presses the stop away from the bolting plate 50. The stop can be formed, for example, by a disk 33 and two counter-nuts 34 and 35 screwed onto the thread of the eye bolt 30. Also a self-locking nut could be used for this purpose. The stop can also be fixedly formed at the support 30, but nuts offer the advantage of better adjustability of the spring tension and facilitate assembly of the holding device.

Figure 2:
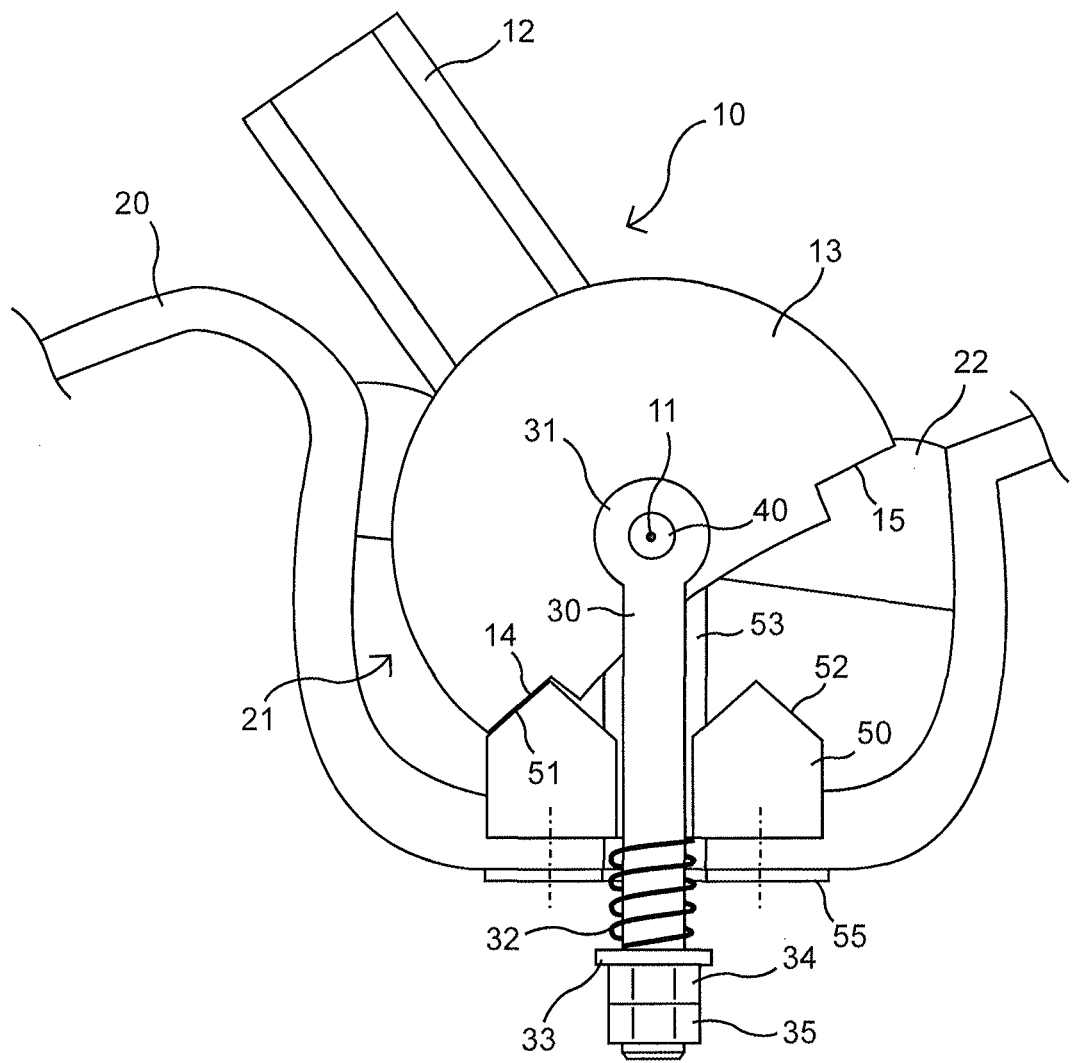
FIG. 2 a schematic section according to FIG. 1, the holder abutting against a second end position.

The spring 32 may be adjacent on the other side to the sheet member 55, the housing 20 or the bolting plate 50. This is substantially dependent on the type of connection between the bolting plate 50 and the housing 20, wherein it has turned out to be of advantage when, as shown in FIG. 2, the spring 32 is guided through the sheet member 55 and the housing 20 and is adjacent to the bolting plate 50. The sub-assembly can then be preassembled and can be guided with the eye bolt 30 through the hole inside the bolting plate 50. Subsequently inside the housing the sheet member 55 is placed and screw-fastened to the housing 20, whereupon the spring 32 can be mounted on the eye bolt 30.

The bolting plate 50 is further configured so that it has two stops 51 and 52 in the form of inclined surfaces. The pivot portion 13 of the holder 10, on the other hand, has corresponding stop faces 14 and 15 contacting the stops 51 and 52 at two defined end positions when the holder 10 is pivoted. For this, the stop faces 14, 15 can be recessed at the outer edges of the pivot area 13 into the same so that there are resulting respective indentations into which corresponding edges of the stop plate 50 fit upon abutment.

FIG. 1 illustrates the holder 10 at a first defined end position at which it is adjacent, by the stop face 15, to the stop 52 of the bolting plate or mounting member 50. When pressure is applied against the holder 10 or a torque is applied to the holder 10, the latter can pivot about the axis of rotation 11 up to the other defined end position shown in FIG. 2. The resilient connection of the holder 10 protects the housing 20 and the holder 10 against damage. Furthermore, the pivot portion 13 can be in the form of a half-shell so that it follows approximately the outer contour of the housing 20 and thus closes the housing 20 to the outside.

Figure 3:
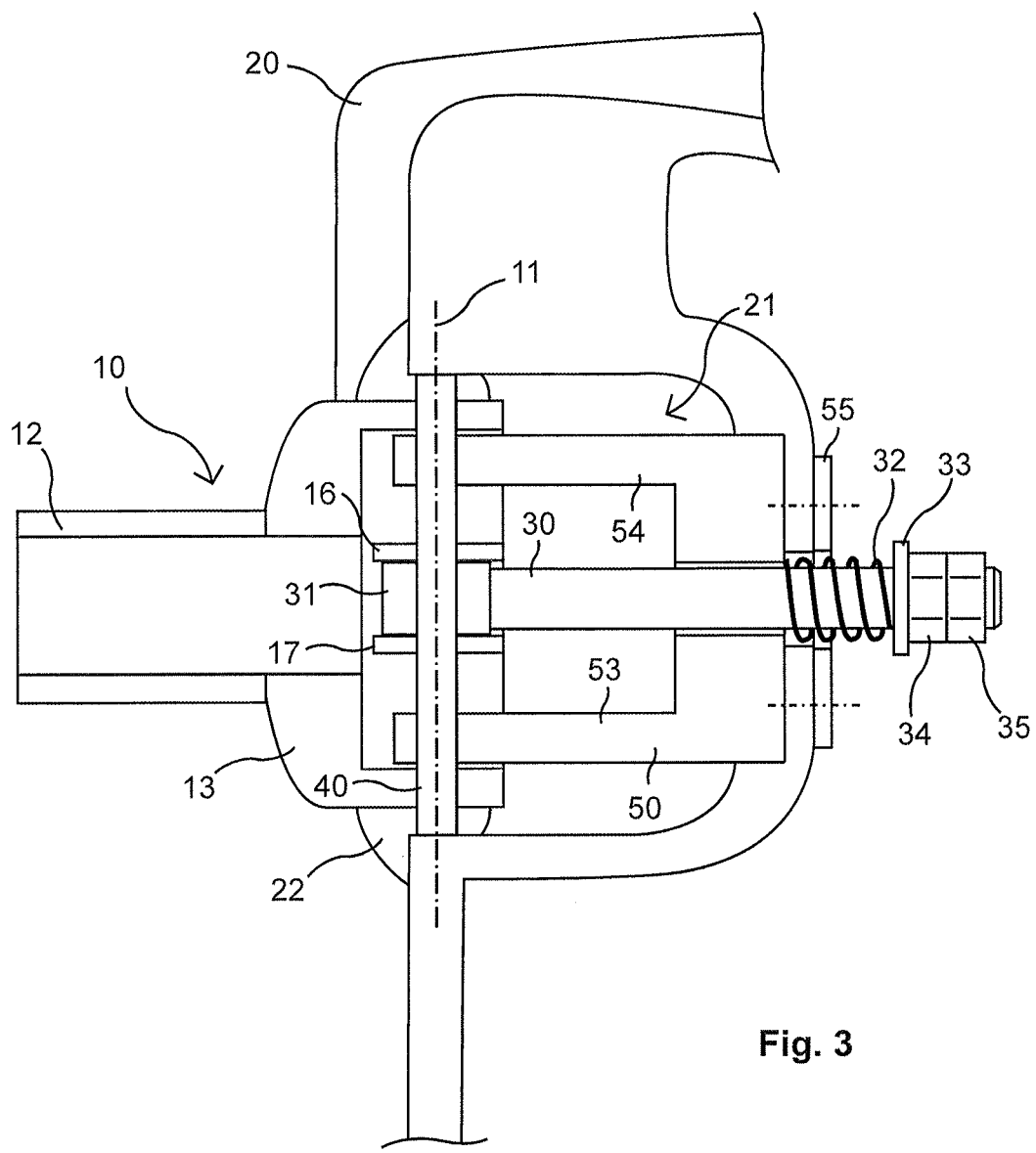
FIG. 3 a schematic section along the pivot axis of the holder according to FIG. 1.

FIG. 3 illustrates a schematic section along the axis of rotation 11 in order to emphasize especially the fixing of the holder 10 at the bolting plate 50 and thus at the housing 20. The eye bolt 30 extends through the bolting plate 50 and on the other side exhibits the eye 31 through which the connecting bolt 40 is guided. The ends of the connecting bolt 40 are guided in two receiving portions 53 and 54 formed at the bolting plate 50 and being provided on opposed sides of the eye bolt 30. A lower one of said receiving portions 53 is also shown in the section of the FIGS. 1 and 2.

Moreover, a friction brake is provided by which pivoting of the holder 10 about the axis of rotation 11 can be decelerated. Said friction brake can be formed at the holder 10 by any component parts that contact fixed components and have an appropriate braking effect. In the embodiment of the figures this is achieved by two plate-shaped braking elements 16 and 17 formed or arranged at the pivot portion 13 of the holder 10. The braking elements 16, 17 are adjacent to the eye 31 of the eye bolt 30 at opposed sides, wherein they extend transversely to the axis of rotation 11. The areas of the braking elements 16, 17 facing the eye 31 can be provided with a surface increasing the friction coefficient.

The invention claimed is:

1. A holding device for a medical device comprising a holder and a second component part by which the holder is coupled or adapted to be coupled, the holder including a receiving portion to which a functional part can be detachably introduced, wherein
the holder further includes a pivot portion by which the holder is pivotably mounted to a support of the second component part so as to be pivotable about an axis of rotation, the support being movable relative to the second component part in a spring-loaded manner; and
the second component part includes a recess inside which the pivot portion and the support are arranged so that when the holder is pivoted about the axis of rotation merely the receiving portion protrudes from the recess, wherein the second component part comprises means by which pivoting of the holder can be delimited between two defined end positions, wherein the holder can be locked in each of the end positions.

2. The holding device according to claim 1, wherein an area between the pivot portion of the holder and the recess is bridged by a cover.

3. The holding device according to claim 1, wherein the holder can be locked in each of the end positions.

4. The holding device according to claim 1, wherein two stops which at the two defined end positions contact respective stop faces at the pivot portion of the holder are formed at the second component part.

5. The holding device according to claim 1, wherein a friction brake is provided for decelerating the pivoting motion of the holder about the axis of rotation.

6. The holding device according to claim 5, wherein at the pivot portion at least two braking elements are formed so that they are in permanent contact with the support upon pivoting the holder, wherein the braking elements are adjacent to the support on two opposed sides.

7. A medical device for extracorporeal blood treatment comprising a housing and a holding device according to claim 1.

8. The medical device according to claim 7, wherein the functional part is a dialyzer or a holder for accommodating a dialyzer.

9. A holding device for a medical device comprising a holder and a second component part by which the holder is coupled or adapted to be coupled, the holder including a receiving portion to which a functional part can be detachably introduced, wherein
the holder further includes a pivot portion by which the holder is pivotably mounted to a support of the second component part so as to be pivotable about an axis of rotation, the support being movable relative to the second component part in a spring-loaded manner, wherein the holder is pivotably mounted to the second component part via a pivot bolt guided through an eye of the support, wherein each of the two end portions of the pivot bolt is introduced in a respective receiving portion at the second component part; and
the second component part includes a recess inside which the pivot portion and the support are arranged so that when the holder is pivoted about the axis of rotation merely the receiving portion protrudes from the recess.

10. The holding device according to claim 9, wherein the receiving portions are provided at a mounting member detachably arranged on the second component part.

* * * * *